(12) United States Patent
Goodwin et al.

(10) Patent No.: US 7,456,019 B2
(45) Date of Patent: Nov. 25, 2008

(54) THREE-DIMENSIONAL CELL TO TISSUE DEVELOPMENT PROCESS

(75) Inventors: Thomas J. Goodwin, Kemah, TX (US); Clayton R. Parker, Safety Harbor, FL (US)

(73) Assignees: Regenetech, Inc., Sugar Land, TX (US); The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 187 days.

(21) Appl. No.: 11/169,385

(22) Filed: Jun. 29, 2005

(65) Prior Publication Data

US 2006/0240550 A1    Oct. 26, 2006

(51) Int. Cl.
*C12N 5/02* (2006.01)
(52) U.S. Cl. .................................. 435/394; 435/173.1
(58) Field of Classification Search ........................ None
See application file for complete search history.

(56) References Cited

U.S. PATENT DOCUMENTS

| | | | |
|---|---|---|---|
| 5,030,225 A | 7/1991 | Aebischer et al. |
| 5,153,132 A | 10/1992 | Goodwin et al. |
| 5,153,133 A | 10/1992 | Schwarz et al. |
| 5,155,034 A | 10/1992 | Wolf et al. |
| 5,155,035 A | 10/1992 | Schwarz et al. |
| 5,496,722 A | 3/1996 | Goodwin et al. |
| 5,541,103 A | 7/1996 | Kanz et al. |
| 5,599,705 A | 2/1997 | Cameron |
| 5,622,857 A | 4/1997 | Goffe |
| 5,627,021 A | 5/1997 | Goodwin et al. |
| 5,635,387 A | 6/1997 | Fei et al. |
| 5,688,687 A | 11/1997 | Palsson et al. |
| 5,702,941 A | 12/1997 | Schwarz |
| 5,753,506 A | 5/1998 | Johe |
| 5,846,807 A | 12/1998 | Goodwin |
| 5,851,816 A | 12/1998 | Goodwin et al. |
| 5,858,783 A | 1/1999 | Goodwin et al. |
| 5,922,597 A | 7/1999 | Verfaillie et al. |
| 5,985,653 A | 11/1999 | Armstrong et al. |
| 5,994,129 A | 11/1999 | Armstrong et al. |
| 6,008,010 A | 12/1999 | Greenberger et al. |
| 6,048,721 A | 4/2000 | Armstrong et al. |
| 6,096,532 A | 8/2000 | Armstrong et al. |
| 6,117,674 A | 9/2000 | Goodwin et al. |
| 6,129,911 A | 10/2000 | Faris |
| 6,238,908 B1 | 5/2001 | Armstrong et al. |
| 6,238,922 B1 | 5/2001 | Uchida |
| 6,485,963 B1 | 11/2002 | Wolf et al. |
| 2002/0001826 A1 | 1/2002 | Wager et al. |

OTHER PUBLICATIONS

Block I et al, "Gravisensitivity of the Acellular, Slime, Mold, Physarum, Polycephalum Demonstrated on the Fast Rotating Clinostat," European Journal of Cell Biology 41, pp. 44-50, 1986.

Cherry RS et al, "Physical Mechanisms of Cell Damage in Microcarrier Cell Culture Bioreactors," Biotechnology and Bioengineering, vol. 32, pp. 1001-1014 (1988).

Katayama Y et al, "Chromosome analysis after ex vivo expansion of CD34+ cells from human cord blood," Cancer Genetics and Cytogenetics, vol. 125, No. 2, Mar. 2001, pp. 161-162.

Sutherland RM, "Cell and Environment Interactions in Tumor Microregions: The Multicell Spheroid Model," Science 240:177-184 (1988).

*Primary Examiner*—James S Ketter
(74) *Attorney, Agent, or Firm*—Ladas & Parry LLP

(57) ABSTRACT

An improved three-dimensional cell to tissue development process using a specific time varying electromagnetic force, pulsed, square wave, with minimum fluid shear stress, freedom for 3-dimensional spatial orientation of the suspended particles and localization of particles with differing or similar sedimentation properties in a similar spatial region.

22 Claims, 7 Drawing Sheets

THREE-DIMENSIONAL CELL TO TISSUE DEVELOPMENT PROCESS

ORIGIN OF THE INVENTION

The invention described herein was made in part by an employee of the United States Government and may be manufactured and used by and for the Government of the United States for governmental purposes without the payment of any royalties thereon of therefor.

FIELD OF THE INVENTION

The present invention relates to a 3-dimensional cell to tissue and maintenance process, more particularly to methods of culturing cells in a culture environment, either in space or in a gravity field, with minimum fluid shear stress, freedom for 3-dimensional spatial orientation of the suspended particles and localization of particles with differing or similar sedimentation properties in a similar spatial region. The process is a dramatic improvement over prior processes in that the production rate and amount is significantly increased by applying a time varying electromagnetic force of from about 0.05 gauss to 0.5 gauss to the culture environment during the culturing of the cells.

BACKGROUND OF THE INVENTION

Cell culture processes have been developed for the growth of single cell bacteria, yeast and molds which are resistant to environmental stresses or are encased with a tough cell wall. Mammalian cell culture, however, is much more complex because such cells are more delicate and have more complex nutrient and other environmental requirements in order to maintain viability and cell growth. Large-scale cultures of bacterial type cells are highly developed and such culture processes are less demanding and are not as difficult to cultivate as mammalian cells. These techniques are highly empirical and a firm theoretical basis is not developed. Bacterial cells can be grown in large volumes of liquid medium and can be vigorously agitated without any significant damage. Mammalian cells, on the other hand, cannot withstand excessive turbulent action without damage to the cells and must be provided with a complex nutrient medium to support growth.

In addition, mammalian cells have other special requirements; in particular most animal cells must attach themselves to some substrate surface to remain viable and to duplicate. On a small scale, mammalian cells have been grown in containers with small microwells to provide surface anchors for the cells. However, cell culture processes for mammalian cells in such microwell containers generally do not provide sufficient surface area to grow mammalian cells on a sufficiently large scale basis for many commercial or research applications. To provide greater surface areas, microcarrier beads have been developed for providing increased surface areas for the cultured cells to attach. Microcarrier beads with attached cultured cells require agitation in a conventional bioreactor vessel to provide suspension of the cells, distribution of fresh nutrients, and removal of metabolic waste products. To obtain agitation, such bioreactor vessels have used internal propellers or movable mechanical agitation devices which are motor driven so that the moving parts within a vessel cause agitation in the fluid medium for the suspension of the microcarrier beads and attached cells. Agitation of mammalian cells, however, subjects them to high degrees of shear stress that can damage the cells and limit ordered assembly of these cells according to cell derived energy. These shear stresses arise when the fluid media has significant relative motion with respect to vessel walls, impellers, or other vessel components. Cells may also be damaged in bioreactor vessels with internal moving parts if the cells or beads with cells attached collide with one another or vessel components.

In addition to the drawbacks of cell damage, bioreactors and other methods of culturing mammalian cells are also very limited in their ability to provide conditions that allow cells to assemble into tissues that simulate the spatial 3-dimensional form of actual tissues in the intact organism. Conventional tissue culture processes limit, for similar reasons, the capacity for cultured tissues to express a highly functionally specialized or differentiated state considered crucial for mammalian cell differentiation and secretion of specialized biologically active molecules of research and pharmaceutical interest. Unlike microorganisms, the cells of higher organisms such as mammals form themselves into high order multicellular tissues. Although the exact mechanisms of this self-assembly are not known, in the cases that have been studied thus far, development of cells into tissues has been found to be dependent on orientation of the cells with respect to each other (the same or different type of cell) or other anchorage substrate and/or the presence or absence of certain substances (factors) such as hormones, autocrines, or paracrines. In summary, no conventional culture process is capable of simultaneously achieving sufficiently low shear stress, sufficient 3-dimensional spatial freedom, and sufficiently long periods for critical cell interactions (with each other or substrates) to allow excellent modeling of in vivo tissue structure.

U.S. Pat. No. 5,155,035, Wolf et al., provides a method that overcomes prior problems without subjecting the cells to destructive amounts of shear, but the production rate of such process is insufficiently low to be of substantial commercial value. The current invention improves on that process by subjecting the culture medium to a time varying electromagnetic force to increase the production rate to commercially significant levels.

A paper entitled: "The Clinostat—A Tool For Analyzing The Influence of Acceleration On Solid-Liquid Systems" by W. Briegleb, published by the proceedings of a workshop on Space biology, Cologne Germany, on Mar. 11, 1983, (ES-ASP-206, May 1983). In this paper, clinostat principles are described and analyzed relative to gravity affects. Some clinostat experiments are described including experiments where monocellular suspended organisms (protozoans) are placed within cylinders which are rotated about a horizontal axis.

A paper entitled, "The Large-Scale Cultivation of Mammalian Cells", by Joseph Feder and William R. Tolbert, published in the Scientific American, January 1983, Vol. 248, No. 1. Pgs. 36-43. In this paper, agitation of the cells is described as required to keep the cells suspended in the medium and describes a turbine agitator, a marine propeller agitator, and a vibrating mixer for mixing. The paper also describes a perfusion reactor in which four slowly rotating flexible sheets of monofilament nylon provide agitation The sheets are rotated about a vertical axis while the medium in the main vessel is continuously pumped to the satellite filter vessel. The filter retains the cells which are pumped along with the remainder medium back into the vessel for further proliferation. A paper entitled, "Large Scale Cell Culture Technology", William R. Tolbert, Joseph Feder, Monsanto Company, St. Louis, Mo., Annual Reports on Fermentation Processes, Vol. 6, 1983, discloses a flat plate hollow fiber system of high culture surface area described as allowing culture of anchorage dependent cells and accumulation of cell secretor products. A culture vessel with flexible spiral vanes for suspension of microcarriers and a fluidized bed with media perfusion is described.

A paper entitled, "Gravisensitivity of the Acellular, Slime, Mold, Physarum, Polycephalum Demonstrated on the Fast Rotating Clinostat", by Ingrid Block and Wolfgang Brigley, published in the European Journal of Cell Biology 41, Pgs. 44-50, 1986. This paper described rotation of a culture vessel about a horizontal axis for the simulation of weightlessness.

A paper entitled, "Cell and Environment Interactions in Tumor Microregions: The Multicell Spheroid Model"; by Robert M. Sutherland, Science 240: 177-184; (1988) discloses the use of multicell spheroids, without attachment substrates, of tumor cells to study cell and environment interactions in tumors. Conventional culture, processes are utilized to produce limited size and viable tumor cell aggregates.

Cell cultures from various bio-reactors, including a prototype of a slow turning lateral vessel (STLV) designed for batch culturing of cells were presented at a poster session at the First Canadian Workshop on R & D Opportunities on Board the Space Station, National Research Council Canada, May 6-8, 1987, Ottawa, Canada, and published in the Proceedings "Spacebound '87", as a paper entitled "Growth and Maintenance of Anchorage Dependent Cells in Zero Headspace Bioreactor Systems Designed For Microgravity", by Lewis et al.

A paper entitled, "Physical Mechanisms of Cell Damage in Microcarrier Cell Culture Bioreactors", Robert S. Cherry and Eleftherios Terry Poportsakis, Biotechnology and Bioengineering, Vol. 32, Pp. 1001-1014 (1988) discloses mechanisms for damage of anchorage dependent cells cultured on microcarrier beads. Bridging of cells across beads to form bead aggregates is described as a damage mechanism due to breaking of these bridges from mechanical mechanisms.

SUMMARY OF THE INVENTION

The process of the present invention provides methods for enhancing the culture of cells and living 3-dimensional tissues by controlling the fluid mechanical environment to achieve the desired culture characteristics. More specifically, the process of the present invention allows enhanced capability to simultaneously achieve a culture environment with reduced fluid shear stress, freedom for 3-dimensional spatial orientation (of suspended particles), and localization of particles with differing (or similar) sedimentation properties in a similar spatial region (collocation). This enhanced culture process allows orderly assembly of cells and attachment substrates into higher order tissue-like structures. Carrying out the culture process of the present invention in reduced gravity, as in space, allows an immense expansion of these operating limitations. However even in unit gravity the process of this invention allows a large improvement over conventional culture processes for typical tissues of interest. The minimal fluid shear stress obtainable in unit gravity is determined by the gravitationally induced motion of the suspended particles through the culture medium and is far less in the process of the present invention than that obtainable by culture processes heretofore used. Of critical importance to this invention is subjecting the culture to a time varying electromagnetic force (pulsed, square wave) of from about 0.05 to 0.5 gauss during the culture process.

A 3-dimensional culture environment which initially is controlled to have essentially no fluid shear stress which is part of the process of the present invention allows higher densities of healthy living cells and allows the maintenance or growth of cells into higher order 3-dimensional multicellular tissue-like structures with larger size, improved viability, and finer delicate structure than other culturing processes. These cultured tissues are higher fidelity models of the actual in vivo tissue and are therefore important for research and clinical applications. In addition delicate cell types may be cultured with improved viability with the processes of the present invention. In the process of the present invention, higher levels of cell and tissue differentiation may be obtained by allowing freedom for the spatial orientation of cells with respect to each other, exchange of soluble chemical signals, intercellular mechanical signals, cellular to insoluble substrate interactions, and expression of the tissue differentiation state resulting from these inductive mechanisms. Subjecting the cells to the specified time varying electromagnetic force dramatically increases the cell growth and differentiation to an extent that the cell production becomes commercially important.

The minimal shear stress level obtainable in unit gravity is obtained when the fluid medium, vessel wall, and internal vessel components are caused to rotate at the same angular rates. The absolute angular rotation rate is chosen to produce the desired orbital path of cells, tissues, and substrates through the fluid medium. This path is primarily determined by the sedimentation properties of these suspended particles (through the culture medium), the external gravitational field strength (and direction), angular rotational rates, and vessel dimensions. These parameters are related by the appended fluid dynamic calculations that may be utilized to choose optimal rotation rates and vessel dimensions for specific cultured tissues and culture fluid mediums of various viscosities. In a specific process, the fluid-culture medium is caused to rotate about a horizontal (or nearly horizontal) axis with respect to the external gravity vector at an angular rate which optimizes the orbital path of cells, tissues, and attachment substrates suspended within this culture medium so as to optimally control collision frequencies, collision intensities, and localization of these particles with themselves and with the limiting boundaries of the culture vessel. The vessel walls are set in motion relative to the fluid medium and internal vessel components so as to introduce initially essentially no fluid shear field; however, when appropriate to produce the desired multicellular assemblies or for the specific research purpose, such as studying the effects of shear on the 3-dimensional tissue, a shear field may be introduced and controlled.

DETAILED DESCRIPTION OF THE INVENTION

Figure 1:
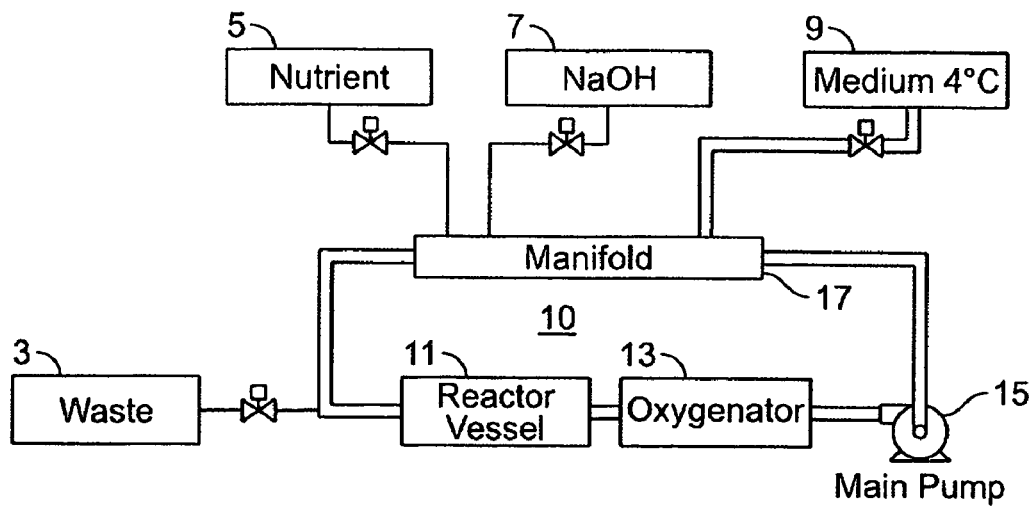
FIG. 1 schematically illustrates one apparatus which may be utilized in the present invention.

The process of the present invention optimizes a group of culture environmental conditions, even as the culturing progresses, in a manner that greatly enhances the capability to form and maintain 3-dimensional living tissues. The 3-dimensional living tissues are formed and maintained from cells, which is used herein to include cells in any form, for example, individual cells or tissue or dissociated source cells or cells pre-attached to substrates or intact tissue resections. The process simultaneously minimizes the fluid shear stress, provides 3-dimensional freedom for cell and substrate spatial orientation, and increases localization of cells, tissues, and substrates in a similar spatial region for significant periods during the cell culture. The process of the present invention provides these three criteria that are hereinafter referred to as "the three criteria above". Transient disruptions of the stabilized environment are permitted and are tolerated for logistical purposes during initial system priming, sample acquisition, system maintenance, and culture termination. The cultured 3-dimensional tissues (and substrates) increase in size as the culture progresses necessitating appropriate adjustment of rotational rates. The extent or amount of adjustment, depending on vessel dimensions, external gravitational strength, and absolute sedimentation rate of particles through the media is made in order to optimize these particle paths. Increased external gravity field strength and increased tissue (and substrate) sedimentation rate induce restrictions on the choice of parameters, particularly rotational rate, which ultimately limits the useful operating range of the process. These same factors place a lower limit on the shear stress obtainable, even within the process operating range, due to gravitationally induced drift of the particles through the culture media. Calculations and measurements place this minimum shear stress very nearly to that resulting from the particles terminal sedimentation velocity (through the culture media) for the external gravity field strength. Centrifugal and coriolis induced motion [classical angular kinematics provide the following equation relating the Coriolis force to an object's mass (m), its velocity in a rotating frame ($v_r$) and the angular velocity of the rotating frame of reference ($\square$): $F_{Coriolis} = -2 m (w \times v_r)$] along with secondary effects due to particle and fluid interactions act to further degrade the shear stress level as the growing tissue increases in size. The process of the present invention thus provides an optimization for culturing cells, and 3-dimensionality for spatial orientation of cells, substrates, and tissues. The process further provides for selecting vessel dimensions and rotational rates which minimize collisions of the cultured particles with vessel walls or internal components. Again, increased gravity and particle sedimentation rate (which is proportional to size in all cases in our experience) cause restrictions to the process operating range in terms of maintaining 3-dimensional freedom.

The particular paths which result from rotation of cells, tissues, and substrates about an axis nearly perpendicular to gravity results in these particles, which may differ greatly in sedimentation rates, to remain spatially localized in similar regions for extended periods of time. Those time periods may vary from seconds (when sedimentation characteristics are large) to hours (when sedimentation differences are small). In the process of the present invention this time is extended as compared to conventional techniques. This allows these particles sufficient time to interact as necessary to form multicellular structures and to associate with each other. The ability to retain this spatial approximation of particles, which may differ in sedimentation properties, is degraded by increasing gravity and by increasing particle sedimentation rate. In all of the "three criteria above"; minimizing fluid shear stress, maintaining 3-dimensional freedom for spatial orientation, and maximizing spatial approximation of particles with differing sedimentation properties, a degradation of performance is observed with increasing external gravitational field strength and with increasing particle sedimentation rate. The process of the present invention provides these three criteria above in a manner heretofore not obtained and optimizes the culture environment. It is therefore clear that further enhancement of this process is obtained in a reduced gravity environment.

This process provides the necessary means for support of respiratory gas exchange, supply of nutrients, and removal of metabolic waste products. This is accomplished either by perfusion of media through an external media perfusion loop, direct injection to the culture media, or exchange of these molecules across a diffusion membrane. The atmospheric environment outside the vessel or circulation loop is controlled with respect to temperature, humidity, and gas mixture. This is accomplished by placing the culture and apparatus within a tissue culture incubator.

This cell and tissue culture process provides a stabilized environment into which cells or tissues may be introduced, suspended, assembled, grown, and maintained with improved retention of delicate 3-dimensional structural integrity. The fluid culture media is initially stabilized into near solid body horizontal rotation within the confines of a similarly rotating vessel wall. The slowest RPM is chosen which will be sufficient to produce acceptable particles orbits (with respect to the three criteria above) upon addition of the initial priming load of cells, tissue, and substrates. The initial culture may be primed with metabolically living matter which for example may be separated cells and substrates, cells already attached to substrates, or resections of tissue from donor sources.

The addition or priming of particles, cells or substrates, may be simultaneously or sequentially introduced. In most cases the initial particles with which the culture is primed sediment at a slow rate under 0.1 centimeter per second. It is therefore possible, at this early culture stage, to select from a broad range of rotational rates (typically 5 to 120 RPM) and vessel diameters (typically 0.5 to 36 inches). The slowest rotational rate is advantageous because it minimizes equipment wear and other logistics associated with handling of the culture. A vessel diameter is chosen which has the appropriate volume for the intended quantity of cultured material and which will allow a sufficient seeding density of cells, tissues, and substrates for the availability of these components. The outward particle drift due to centrifugal force is exaggerated at higher vessel radii and for rapidly sedimenting particles. This limits the maximum radius of the rotational culture as a function of the sedimentation properties of the tissues anticipated in the final culture stages (when large tissues with high rates of sedimentation have formed). Selected levels of shear stress may be introduced to the culture environment by differential rotation of vessel components. This is useful to control the rate and size of tissue formation in order to maintain the particle sizes (and associated sedimentation rate) within a range for which the process is able to satisfy the three criteria above.

The presence of particles within the stabilized fluid media causes secondary effects to this fluid. These particles move through the fluid media under the influence of gravity, centrifugal, and coriolus forces. This motion induces secondary motions to the fluid media. The "stabilized fluid media" referred to in this process is that fluid condition, particularly the fluid velocity gradients, prior to introduction of the particles, but which will support a nearly uniform suspension of these particles upon their introduction. Therefore, the significant motion of the fluid media with respect to vessel walls, significant fluid shear stress, and other fluid motions are the result of the presence of these particles within the fluid media. One exception is the case where a fluid velocity gradient and resulting fluid shear stress is intentionally placed on the stabilized fluid for the purpose of limiting the rate or ultimate size of tissue assembly, or for shear stress research purposes.

Figure 5:
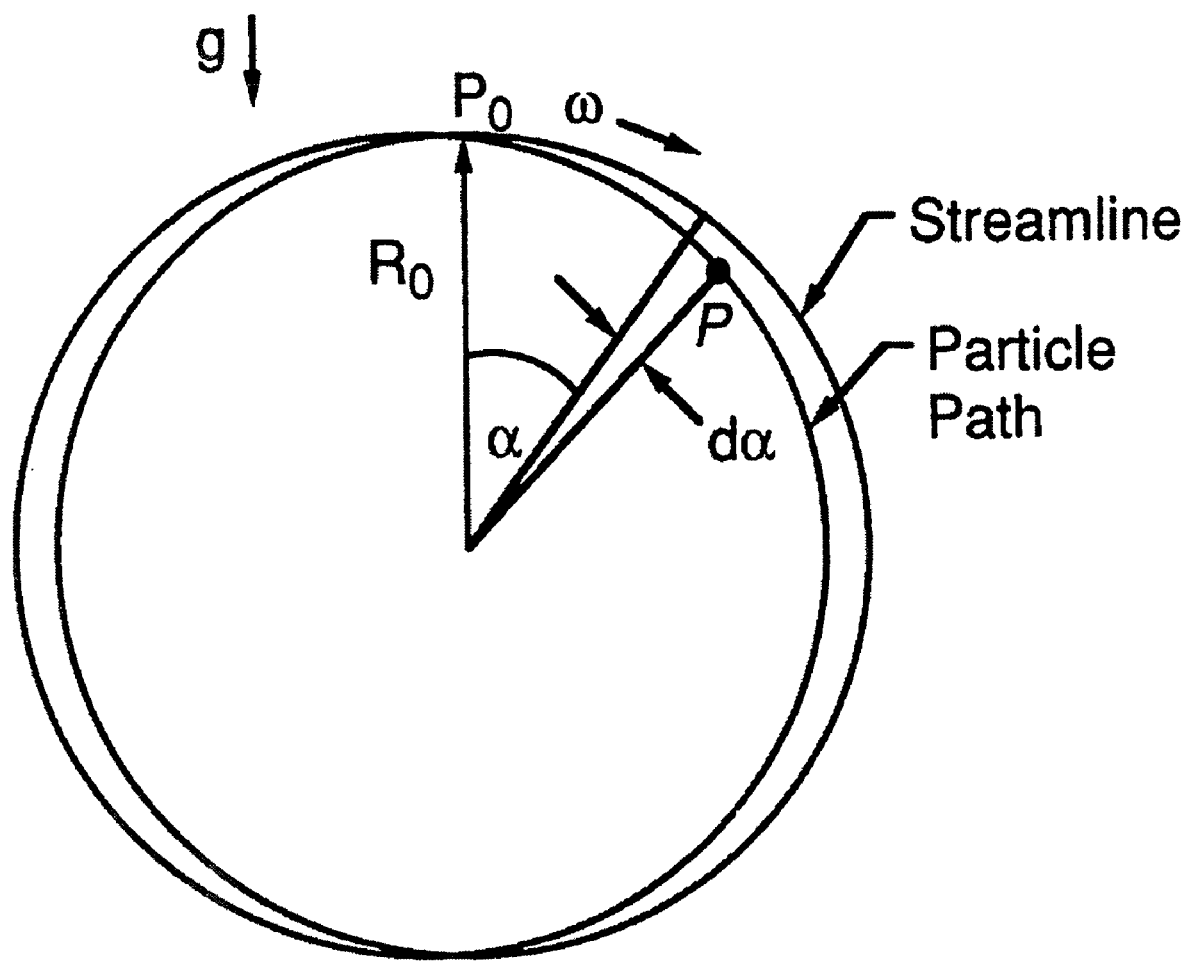
FIG. 5 is the orbital path of a typical assembled tissue particle in the non-rotating reference frame.
Figure 6:
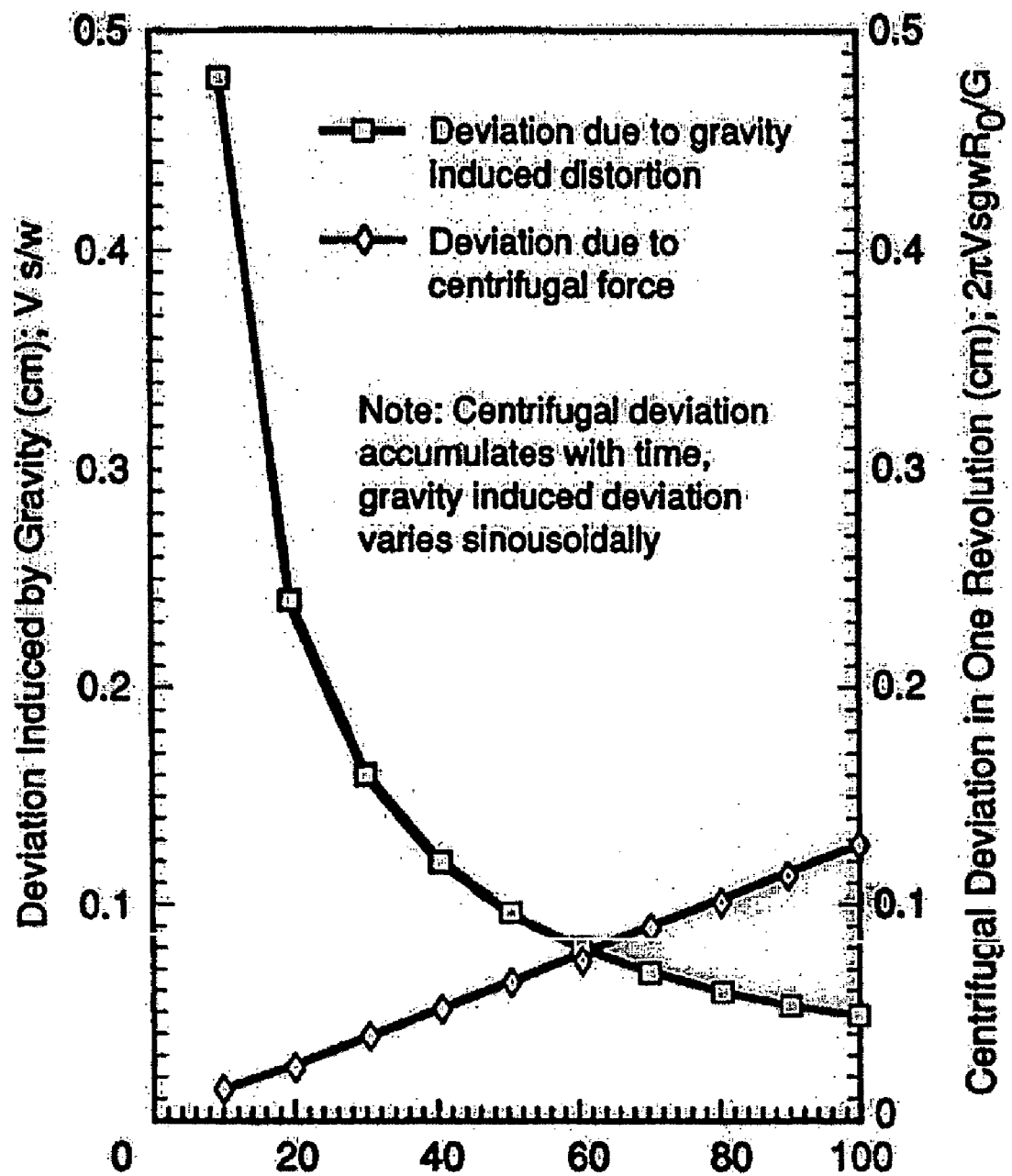
FIG. 6 is a graph of the magnitude of deviation of an assembled tissue particle per revolution.

The path of the particles has been analytically calculated in terms of the physical variables important to this tissue culture process. These variables are the vessel dimensions, fluid rotational rate, external gravitational field strength, and particle sedimentation rate. The analysis incorporates the particle motion resulting from gravity, centrifugation, and coriolus effects. A computer simulation of these governing equations allows the operator to model the process and select parameters acceptable (or optimal) for the particular planned tissue culture. FIG. 5 shows the typical shape of the particle orbit as observed from the external (non-rotating) reference frame. FIG. 5 is a graph of the radial deviation of a particle from the ideal circular streamline plotted as a function of RPM (for a typical particle sedimenting at 0.5 cm per second terminal velocity). This graph (FIG. 6) shows the decreasing amplitude of the sinusoidally varying radial particle deviation as induced by gravitational sedimentation. FIG. 6 also shows increasing radial particle deviation (per revolution) due to centrifugation as RPM is increased. These opposing constraints necessitate carefully choosing the optimal RPM to minimize particle impacts with, or accumulation at the vessel walls. A family of curves is generated which is increasingly restrictive, in terms of workable RPM selections, as the external gravity field strength is increased or the particle sedimentation rate is increased. This family of curves, or preferably the computer model which solves these governing orbit equations, is utilized to select the optimal RPM and vessel dimensions for culture of particles of a given sedimentation rate in a given external gravity field strength. As a typical culture progresses the tissues increase in size and sedimentation rate therefore necessitating frequent re-selection of the optimal rotation rate.

Figure 7:
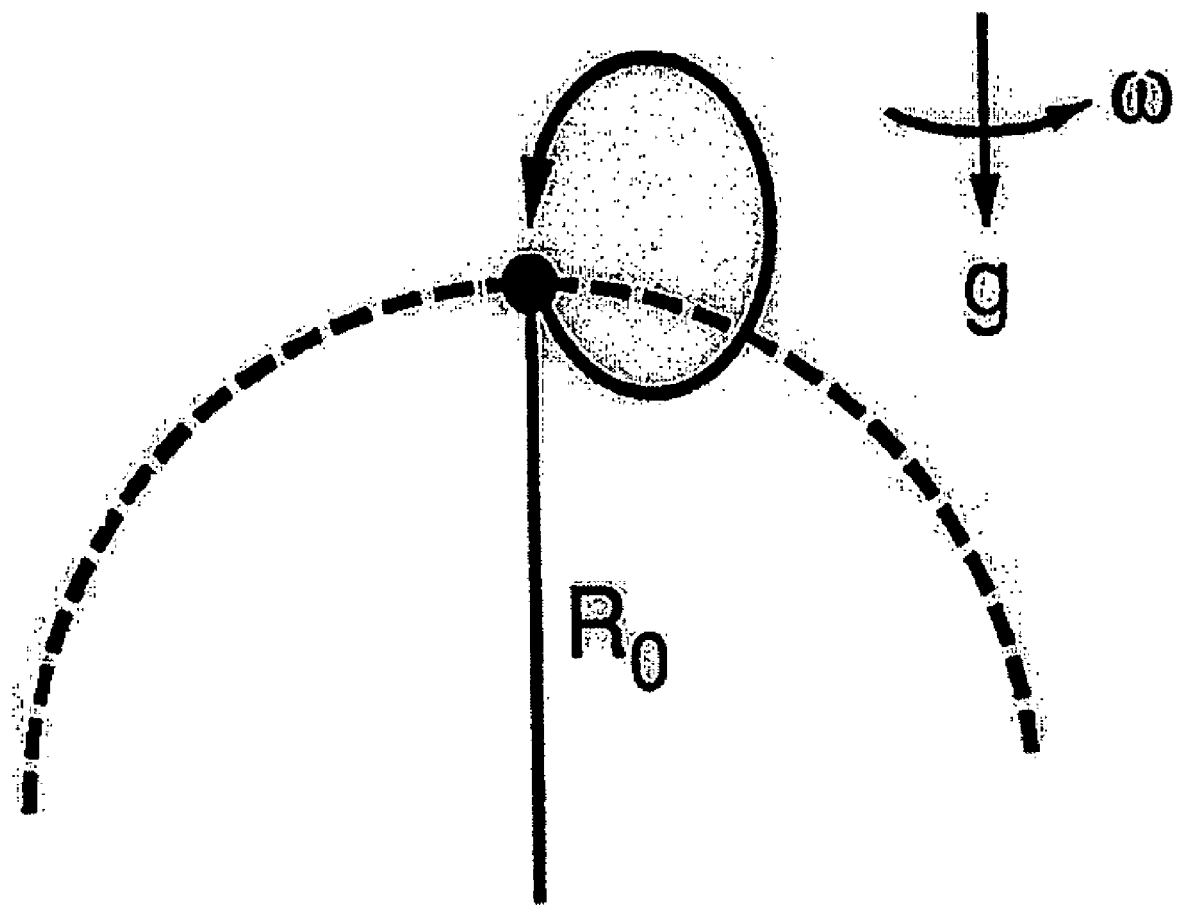
FIG. 7 is a representative particle path as observed in the rotating reference frame of the rotating fluid media.

A gross determination of corrective rotational rate adjustments in response to visual observations may be made. If the particles are observed to excessively distort inwards on the downward side and outwards on the upwards side then RPM must be increased. If the particles are observed to centrifugate excessively to the outer walls then the RPM must be reduced. As the operating limits are reached in terms of high particle sedimentation rates or high gravity strengths the operator is unable to satisfy both of these conditions and is forced to accept degradation in performance as measured against the three criteria above. If the particle orbit, FIG. 5, is observed from the rotating reference frame of the fluid media it is seen to move in nearly circular path under the influence of the now rotating gravity vector (FIG. 7). The two pseudo forces, coriolis and centrifugal, result from the rotating (accelerated) reference frame and cause distortion of the otherwise nearly circular path. Higher gravity levels and higher particle sedimentation rates produce larger radius circular paths which correspond to larger trajectory deviations from the ideal circular orbit as seen in the non rotating reference frame. In the rotating reference frame it is now apparent that particles of differing sedimentation rates will remain spatially localized near each other for long periods of time with greatly reduced net cumulative separation than if the gravity vector were not rotated. The particles are sedimenting. But they are sedimenting in a small circle (as observed in the rotating reference frame). This allows particles of differing sedimentation properties sufficient time to interact mechanically and through soluble chemical signals. The sedimentation rates of cells, tissues, and substrates for which this process produces significant advantages is from essentially zero up to 10 cm per second. As the external gravity field is reduced it is possible to obtain much denser and larger 3-dimensional structures. In order to obtain the minimal shear stress level it is important that the vessel walls and internal components be rotated at as nearly as possible the same rate as the culture media. This minimizes the fluid velocity gradient induced upon the stabilized fluid media. Fresh or recycled culture media may be moved within the vessel at a rate sufficient to support metabolic gas exchange, nutrient delivery, and metabolic waste product removal. This also will slightly degrade the otherwise quiescent culture environment. In the typical case (a tissue which sediments at 0.5 cm per second) in which 5 ml per minute is perfused through a 500 ml culture vessel an average flow-speed of 0.001 cm per second results. This is quite acceptable and is far slower than either gravitationally or centrifugally induced particle motion. This perfusion rate may be increased as the tissues' metabolic demand increases and a large margin is available before significant fluid shear stress results from this fluid perfusion motion. It is necessary to introduce a mechanism for the support of respiratory gas exchange, nutrient delivery, factor delivery, and metabolic waste product removal in order to provide a long term stable culture environment able to support significant metabolic loads for periods of hours to months.

It is critical that the culture medium be subjected to a time varying electromagnetic force of from about 0.05 to 0.5 gauss during cell growth. The time varying electromagnetic field is applied to enhance tissue growth of the cells inside the rotating wall vessel. The electromagnetic field may be generated by means such as by directing the current wave form through conducting material wrapped around the outside of the rotating wall vessel. The field generation system may either be rotating with the vessel or fixed, and spaced from, the rotating vessel.

The time varying electromagnetic field is produced by a varying electrical potential in the form of a square wave having a frequency of approximately 10 cycles per second. Preferably, a current of about 10 mille-amps, conducted between the wrappings of the conductive material, produces a stimulatory time varying electromagnetic field extending several centimeters from the conductive material. Typically, the range of frequency and oscillating electromagnetic field strength is a parameter, which may be selected for achieving the desired stimulation of particular tissues, cells or genes, and for providing the appropriate amount of up/down regulation of these genes.

In addition to the qualitatively unique tissues that are produced by the process of the present invention an increased efficiency with respect to utilization of the total vessel volume for cell and tissue culture is obtained due to the nearly uniform homogeneous suspension achieved. This allows an increased number of cells or total tissue mass in the same volume reactor with less human resources. Many cell type may be utilized in this process including mammalian, reptile, fish, yeast, and bacteria. The advantage over conventional methods is dependent upon the degree to which 3-dimensional spatial freedom for metabolically active cell interactions, assembly, growth, and maintenance is desired to occur in a low (or controlled) shear rate fluid field. The greatest anticipated advantage is for mammalian cells that are highly shear sensitive and depend greatly on multi-cellular architecture and attachment substrates for their differentiation and function. Fundamental cell and tissue biology research as well as clinical applications requiring accurate in vitro models of in vivo cell behavior are applications for which this process provides an enhancement.

In order to form or to maintain 3-dimensional living tissues from cells or tissue obtained from natural sources this process provides a stabilized quiescent minimal fluid shear stress environment into which cell attachment substrates, structural substrates, and living cells or tissues may be introduced, suspended, assembled, grown, and maintained with retention of delicate 3-dimensional structural integrity. Controlling these particle orbits, particle spatial localizations, and baseline fluid shear rates, by rotation of the culture environment about an axis nearly perpendicular to the gravity vector, produces a process that optimally counteracts the detrimental sedimentation effects, caused by gravity. These effects limit the ability of conventional techniques to simultaneously provide a low fluid shear stress environment, provide 3-dimensional freedom for tissue assembly and maintenance, and to maintain a spatial proximity of particles with differing sedimentation properties.

The process of the present method may be carried out in a number of specific apparatus. One such bioreactor is that described in U.S. Pat. No. 5,155,034 with the bioreactor having a coil wound around it or a coil sleeve placed around it to provide the time varying electromagnetic force.

Referring now to FIG. 1. nutrients 5, acids, bases, or buffers, such as, sodium hydroxide 7 or fresh medium 9. The main pump 15 provides fresh fluid medium to the oxygenator 13 where the fluid medium is oxygenated and passed through the cell culture reactor vessel 11. The waste in the spent fluid medium from the cell culture reactor is removed and delivered to the waste 3 and the remaining fluid medium is returned to the manifold 17 where it receives a fresh charge of nutrients 5, sodium hydroxide 7 or liquid medium 9, as necessary, before recycling by the pump 15 through the oxygenator 13 and to the cell culture reactor vessel 11. Thus, a continuous loop system is provided for the cell growth in the cell culture reactor vessel.

In the main fluid flow loop 10, the culture fluid medium is circulated through the living cell culture in the vessel 11 and around an external life support loop, as shown in the FIG. 1. In this external loop, adjustments are made in response to chemical sensors (not shown) that maintain constant conditions within the cell culture reactor vessel 11. Controlling carbon dioxide pressures and introducing acids or bases correct pH. Oxygen, nitrogen, and carbon dioxide are dissolved in a gas exchange system (not shown) in order to support cell respiration. The closed loop adds oxygen and removes carbon dioxide from a circulating gas capacitance. In this way the minimum amount of stored gases may be taken into space if the device is utilized on a space station or other space vehicles.

Figure 2:
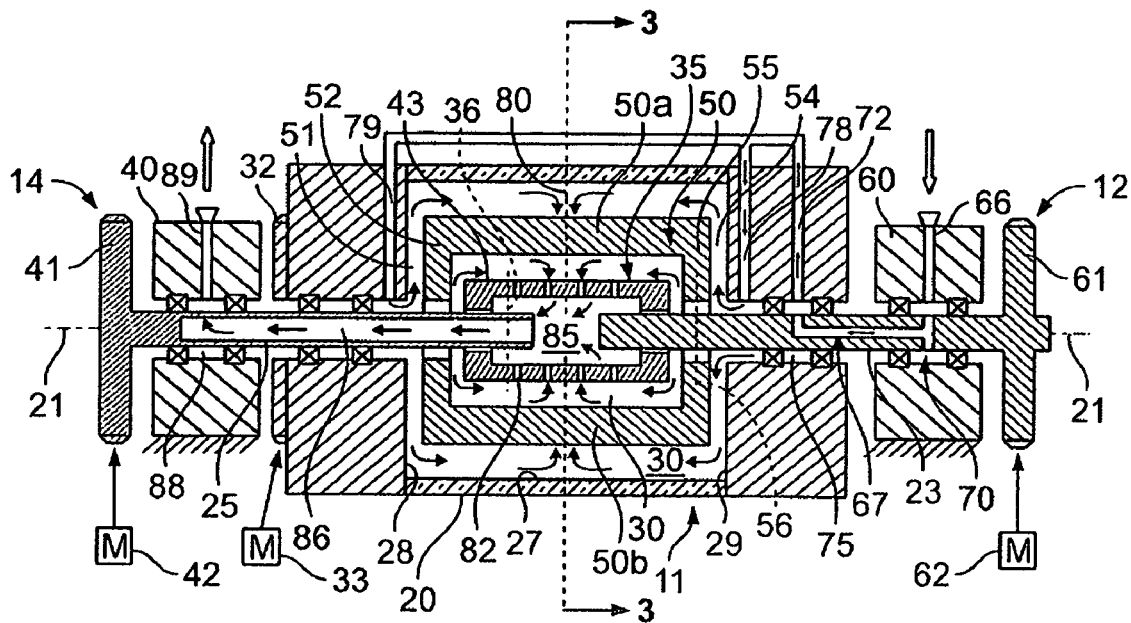
FIG. 2 schematically illustrates the apparatus in FIG. 1 in vertical cross section.
Figure 3:
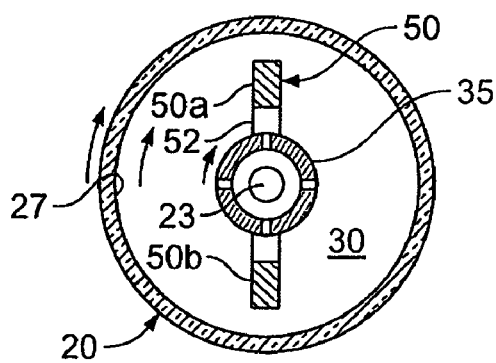
FIG. 3 is a view in cross section along line 3-3 of FIG. 2.

FIGS. 2 and 3 schematically illustrate the general details of a cell culture reactor vessel 11 having an input end 12 and an output end 14 which illustrates the present invention. In FIGS. 2 and 3, an outer tubular housing 20 is rotatably supported for rotation about a horizontal central axis 21 and about an input shaft 23 and an output shaft 25 which are aligned with the central axis 21. The outer tubular housing 20 has a cylindrically shaped interior wall 27, an output transverse end wall 28, and an input traverse end wall 29 that generally define a cylindrically shaped, elongated cell culture chamber 30. A spur gear 32 is attached to one end of the housing 20 and is driven by a motor 33 to rotate the housing about its horizontal central axis 21.

Coaxially disposed about the central axis 21 is a tubular inner filter assembly or member 35 that is rotatably mounted on the input shaft 23 and is coupled (as shown by the dashed line 36) to the output shaft 25. The output shaft 25, in turn, is rotatably supported, in an output stationary housing 40 and the output shaft 25 has an externally located output spur gear 41 which is connected to a drive means 42 for rotating the output shaft 25 and the inner filter assembly 35 independently of the outer housing 20. The annular space between the inner filter assembly 35 and the interior wall 27 of the outer tubular housing 20 define the elongated cell culture chamber 30 located about the horizontal axis 21. Intermediate of the outer wall 43 of the inner filter assembly 35 and the interior wall 27 of the outer housing 20 is an intermediate blade member system 50 which includes two lengthwise extending blade members 50a and 50b which are equiangularly spaced from one another about the central axis 21. Each of the blade members 50a and 50b at a first longitudinal end 51 has a second longitudinal end 54 has a second radial arm 55 which is coupled to the input shaft 23 (shown by dashed line 56). The input shaft 23, in turn, is rotatably mounted in an input stationary housing 60 and the input shaft 23 has an input spur gear 61 that is driven by an independent drive mechanism 62 for rotation of the blade member system 50 independent of the rotation of the outer housing 20.

As shown in FIG. 3, the angular rotation of the three sub-assemblies 20, 35 and 50, i.e., the inner filter assembly or member 35, the outer housing 20, and the intermediate blade member system 50, can be at the same angular rate and in the same direction about a horizontal rotational axis and in the same direction about a horizontal axis so that there is no relative movement between the three sub-assemblies. This condition of operation obtains a clinostat suspension of microcarrier beads in a fluid medium within the cell culture chamber without turbulence.

The rotation of the filter 35 can be started and stopped which will cause the turbulence on the surface of the filter 35 and keep the surface clean. The blade members 50a and 50b assist cell culture as they grow to maintain spatial positions in the rotating fluid medium. This is particularly helpful for higher density culture particles such as bone cells. By rotating the fluid and the outer housing 20, the velocity gradient at the wall boundary layer is nearly eliminated.

Referring again to FIG. 2, fluid medium containing fresh nutrients and gases is input, to an input passageway 66 in the input stationary housing 60 and connects to an input longitudinal passageway 67 in the input shaft 23 by virtue of a sealed input rotative coupling 70. The input passageway 67 in the input shaft 23 couples to a radial supply passageway 72 in an end cap of the outer housing 20 by virtue of a sealed input rotative coupling 75. The radial supply passageway 72, in turn, connects to space apart a radically directed input end input passage 78, and output end input passage 79 in the outer housing 20 where the input end input passage 78, and output end input passage 79 are located at opposite ends of the cell culture chamber 30. As shown by the arrows, when fluid is input at both ends of the cell culture chamber 30, the fluid moves radially outward toward the interior wall 27 of the outer housing 20 and then moves longitudinally in a horizontal direction toward a midpoint plane generally indicated by a vertically dashed line 80 and then moves radially inwardly toward the outer wall 43 of inner filter assembly 35. Thus the fluid in the chamber 30 has a generally toroidal type of motion in radial planes on either side of the midpoint plane 80 of the outer housing 20. The inner filter assembly 35 has apertures 82 along its length for exit passage of fluid and, while not illustrated in FIG. 2, there is a lengthwise extending filter cloth located across the apertures 82 that prevents microcarrier bead members in the chamber 30 from exiting through the apertures 82. Spent fluid in the cell culture chamber 30 thus is passed to the interior 85 of the inner filter assembly 35 and exits via an output longitudinal passageway 86 in the output shaft 25 to an output rotative coupling output 88 in the output stationary housing 40 and to an output passageway 89 to the return of the loop passageway for recharging.

Figure 4:
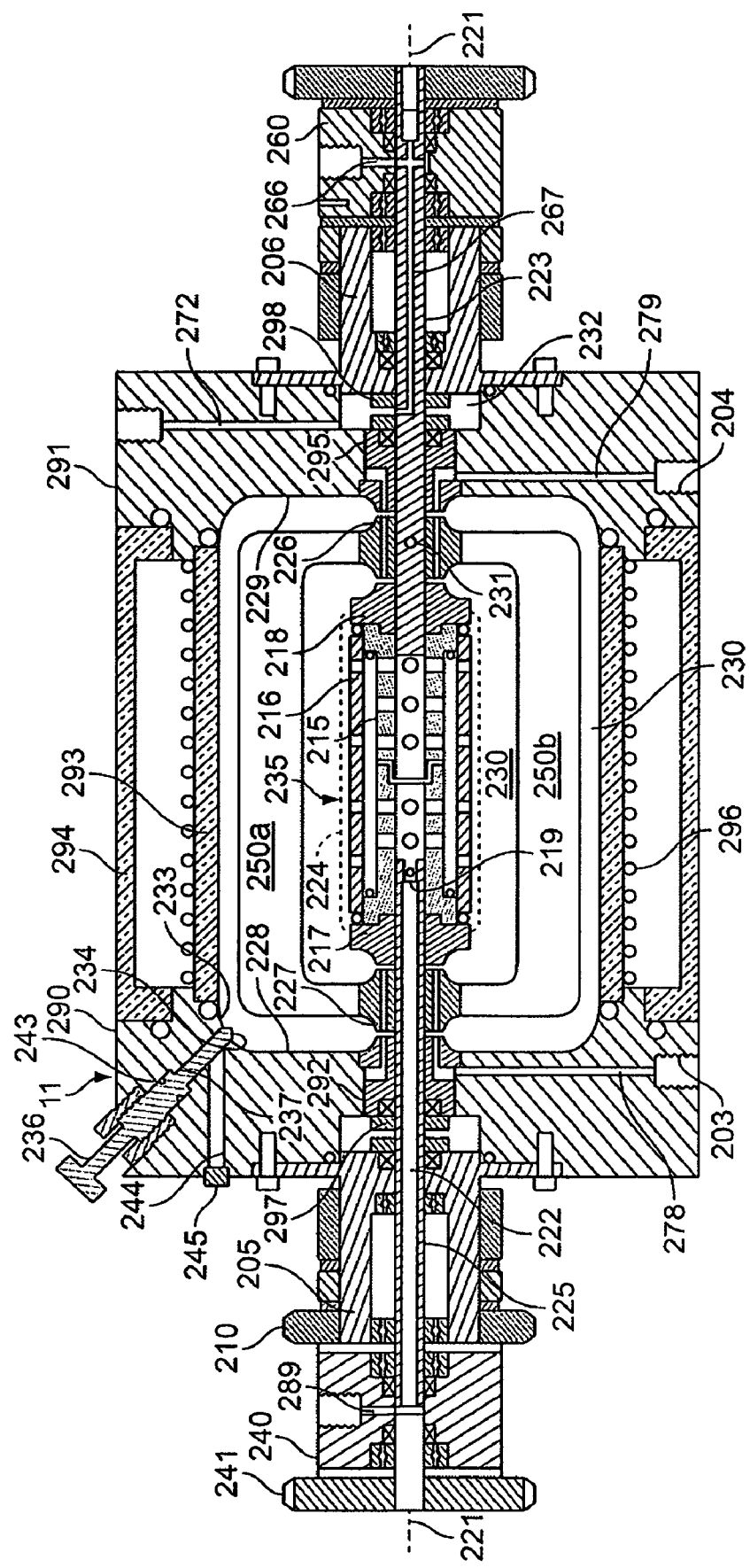
FIG. 4 schematically illustrates the apparatus in FIG. 1 in vertical cross section.
Figure 4A:
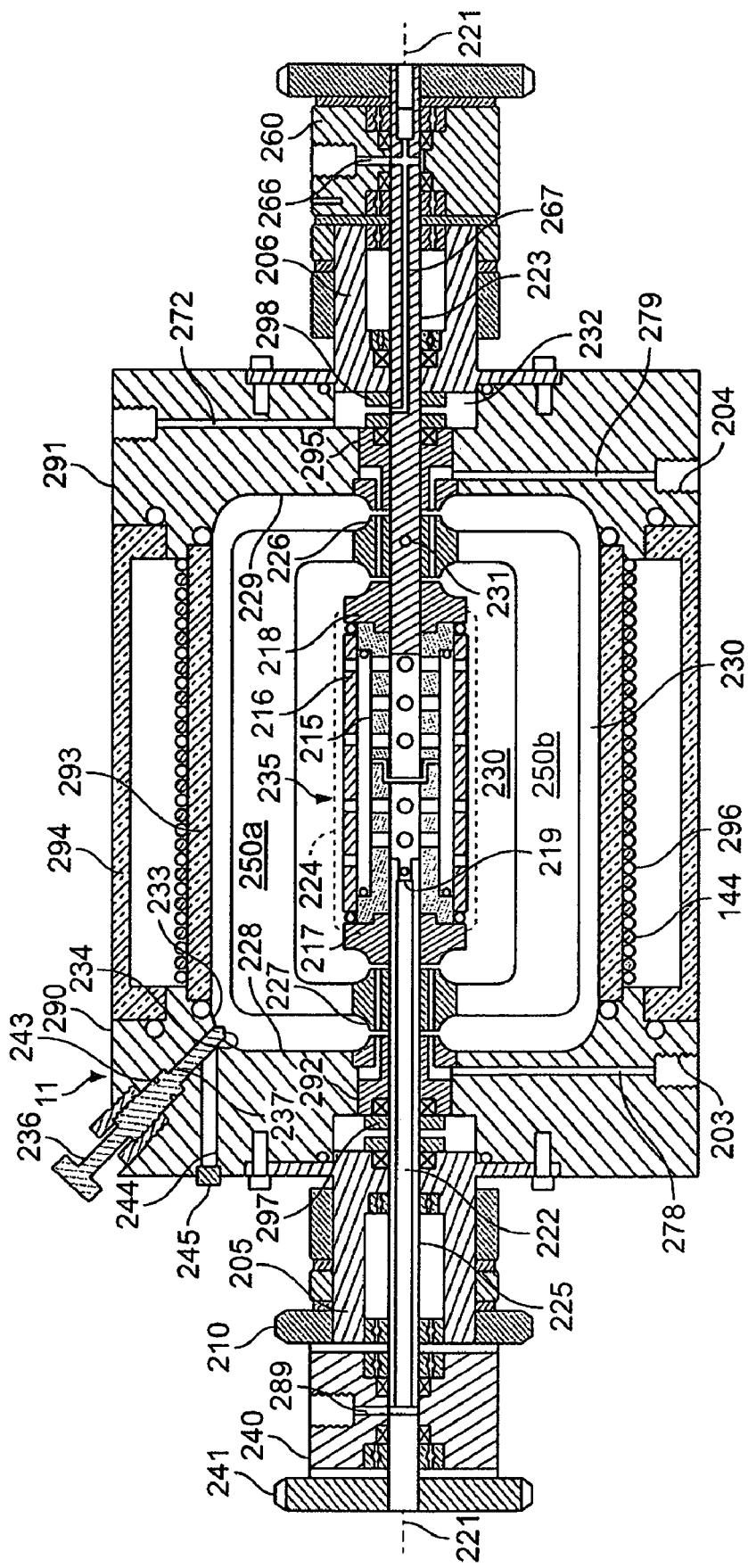
FIG. 4A a cross section as in FIG. 4 showing the addition of a time varying electromagnetic field coil.

Referring now to FIG. 4, a detailed drawing of the reactor vessel 11 of the present invention in a preferred form is illustrated. The outer housing 220 includes a first 290 and second 291 cylindrically shaped transverse end cap members which have facing first 228 and second 229 end surfaces arranged to receive an inner cylindrical tubular glass member 293 and an outer tubular glass member 294. Suitable pressure seals are provided. Between the inner 293 and outer 294 tubular members is an annular wire heater 296 which is utilized for obtaining the proper incubation temperatures for cell growth. The wire heater 296 can be used to also supply a time varying electric field to the culture chamber or, as depicted in FIG. 4A, a separate wire coil 144 can be used to supply the time varying electromagnetic field. The first end cap member 290 and second end cap members 291 have inner curved surfaces adjoining the end surfaces 228, 229 for promoting smoother flow of the fluid within the chamber 230. The first end cap member 290, and second end cap member 291 have a first central fluid transfer journal members 292 and second central fluid transfer journal member 295, respectively, that are rotatably received respectively on an input shaft 223 and an output shaft 225. Each transfer journal member 292, 295 has a flange to seat in a recessed counter bore in an end cap member 290, 291 and is attached by a first lock washer and ring 297, and second lock washer and ring 298 against longitudinal motion relative to a shaft 223, 225. Each journal member 292, 295 has an intermediate annular recess that is connected to longitudinally extending, circumferentially arranged passages. Each annular recess in a journal member 292, 295 is coupled by a first radially disposed passage 278 and second radially disposed passage 279 in an end cap member 290 and 291, respectively, to first input coupling 203 and second input coupling 204. Fluid in a radial passage 278 or 279 flows through a first annular recess and the longitudinal passages in a journal member 292 or 295 to permit access fluid through a journal member 292, 295 to each end of the journal 292, 295 where the access is circumferential about a shaft 223, 225.

Figure 8:
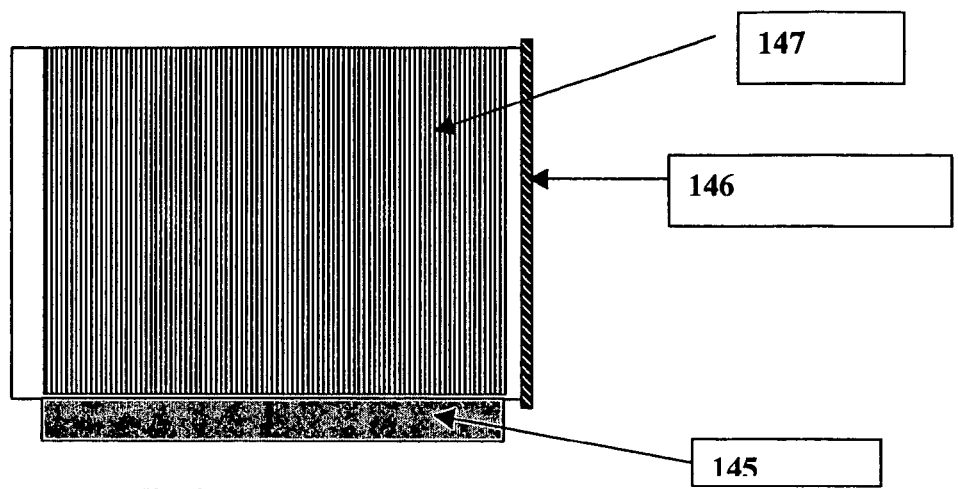
FIG. 8 is a side view of a time varying electromagnetic field coil that can house the entire bioreactor to provide a time varying electromagnetic field within the bioreactor culture chamber.
Figure 9:
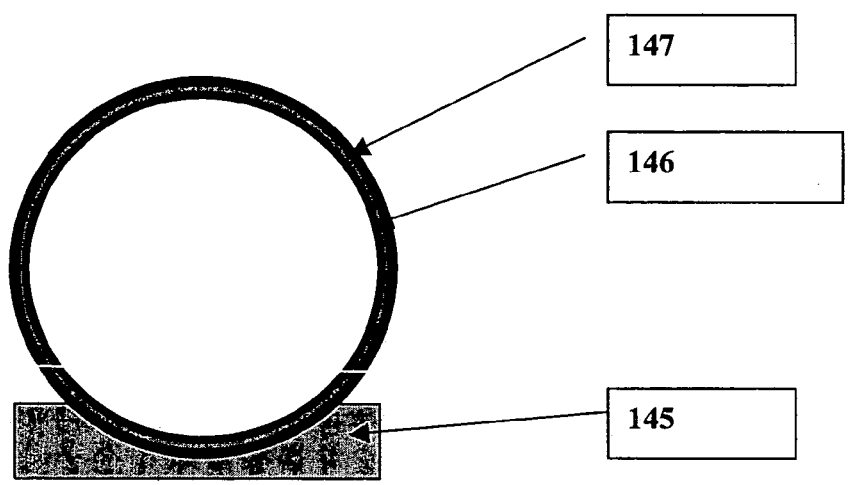
FIG. 9 is an end view of the apparatus shown in FIG. 9.
Figure 10:
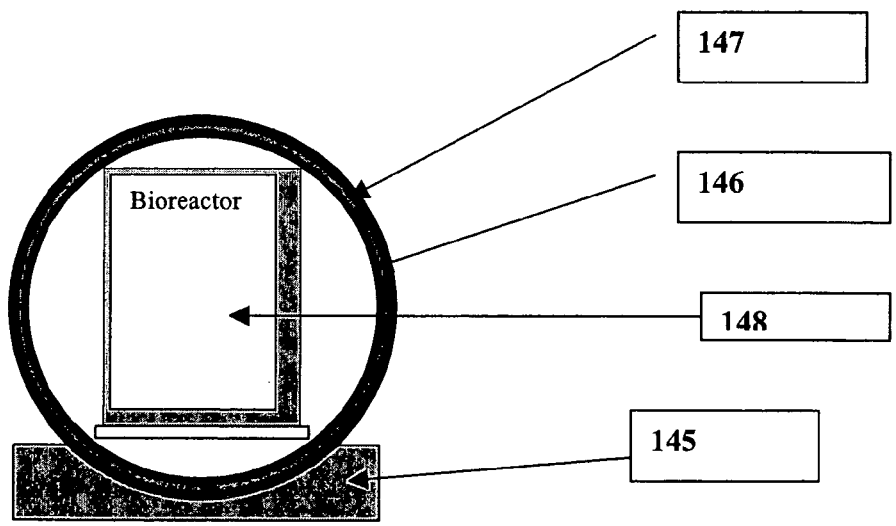
FIG. 10 is an end view of the apparatus shown in FIG. 8 showing the bioreactor therein.

If the time varying electromagnetic force is not applied using the annular wire heater 296, it can be applied by various other methods. For instance, FIG. 8-10 illustrate a device that includes a support base 145, a cylinder coil support 146 supported on the base with a wire coil 147 wrapped around it. The entire bioreactor 148 with the culture chamber is then inserted into the time varying electromagnetic force device.

Referring again to FIG. 4, attached to the end cap members 290 and 291 are a first tubular bearing housings 205, and second tubular bearing housing containing ball bearings which relatively support the outer housing 220 on the input 223 and output 225 shafts. The first bearing housing 205 has an attached first sprocket gear 210 for providing a rotative drive for the outer housing 220 in a rotative direction about the input 223 and output 225 shafts and the central axis 221.

The first bearing housing 205, and second bearing housing 206 also have provisions for electrical take out of the wire heater 296 and any other sensor.

The inner filter assembly 235 includes inner 215 and outer 216 tubular members having perforations or apertures along their lengths and have a first 217 and second 218 inner filter assembly end cap members with perforations. The inner tubular member 215 is constructed in two pieces with an interlocking centrally located coupling section and each piece attached to an end cap 217 or 218. The outer tubular member 216 is mounted between the first 217 and second inner filter assembly end caps.

The end cap members 217, 218 are respectively rotatably supported on the input shaft 223 and the output shaft 225. The inner member 215 is rotatively attached to the output shaft 225 by a pin and an interfitting groove 219. A polyester cloth 224 with a ten-micron weave is disposed over the outer surface of the outer member 216 and attached to O-rings at either end. Because the inner member 215 is attached by a coupling pin to a slot in the output drive shaft 225, the output drive shaft 225 can rotate the inner member 215. The inner member 215 is coupled by the first 217 and second 218 end caps that support the outer member 216. The output shaft 225 is extended through bearings in a first stationary housing 240 and is coupled to a first sprocket gear 241.

As illustrated, the output shaft 225 has a tubular bore 222 that extends from a first port or passageway 289 in the first stationary housing 240 located between seals to the inner member 215 so that a flow of fluid can be exited from the inner member 215 through the stationary housing 240.

Between the first 217 and second 218 end caps for the inner member 235 and the journals 292, 295 in the outer housing 220, are a first 227 and second 226 hubs for the blade members 50a and 50b. The second hub 226 on the input shaft 223 is coupled to the input shaft 223 by a pin 231 so that the second hub 226 rotates with the input shaft 223. Each hub 227, 226 has axially extending passageways for the transmittal of fluid medium through a hub.

The input shaft 223 extends through bearings in the second stationary housing 260 for rotatable support of the input shaft 223. A second longitudinal passageway 267 extends through the input shaft 223 to a location intermediate of retaining washers and rings that are disposed in a second annular recess 232 between the faceplate and the housing 260. A third radial passageway 272 in the second end cap member 291 permits fluid in the recess to exit from the second end cap member 291. While not shown, the third passageway 272 connects through piping and a Y joint to each of the passages 278 and 279. It will be appreciated that there is a substantial symmetry of construction with respect to the vertical plane defined by line 3-3 of FIG. 2.

A sample port is shown in FIG. 4, where a first bore 237 extending along a first axis intersects a corner 233 of the chamber 230 and forms a restricted opening 234. The bore 237 has a counter bore and a threaded ring at one end to threadedly receive a cylindricaly valve member 236. The valve member 236 has a complimentarily formed tip to engage the opening 234 and protrude slightly into the interior of the chamber 230. An O-ring 243 on the valve member 236 provides a seal. A second bore 244 along a second axis intersects the first bore 237 at a location between the O-ring 243 and the opening 234. An elastomer or plastic stopper 245 closes the second bore 244 and can be entered with a hypodermic syringe for removing a sample. To remove a sample, the valve member 236 is backed off to access the opening 234 and the bore 244. A syringe can then be used to extract a sample and the opening 234 can be reclosed. No outside contamination reaches the interior of the vessel 11.

In operation, fluid is input to the second port or passageway 266 to the shaft passageway and thence to the first radially disposed 278 and second radially disposed passageways 279 via the third radial passageway 272. When the fluid enters the chamber 230 via the longitudinal passages in the journals 292, 294 the fluid impinges on an end surface 228, 229 of the hubs 227, 226 and is dispersed radially as well as axially through the passageways in the hubs 227, 226. Fluid passing through the hubs 227, 226 impinges on the end cape members 217, 218 and is dispersed radially. The flow of entry fluid is thus radially outward away from the central axis 221 and flows in a toroidal fashion from each end to exit through the polyester cloth 224 and openings in filter assembly 235 to exit via the passageways 266 and 289. By controlling the rotational speed and direction of rotation of the outer housing 220, chamber 230, and inner filter assembly 235 any desired type of fluid action can be obtained. Of major importance, however, is the fact that a clinostat operation can be obtained together with a continuous supply of fresh medium and oxygen.

PROTOCOL

The methods of the current invention process may be generalized as follows. An appropriate volume rotating wall vessel, such as a 500 ml rotating wall perfused culture vessel with an internal vane, is chosen. The vessel is first connected to the external media perfusion conduits including the gas exchange membranes, pump, and media sample ports and is then sterilized, preferably with ethylene oxide gas, and washed with sterile phosphate buffered saline (PBS) then watered and aerated. The vessel is completely filled with the appropriate media for the cells or tissue to be cultured. The controlled environment incubator that completely surrounds the rotating wall vessel and in which it operates is set for 5% $CO_2$, 21% oxygen, and 37 degrees Celsius. The media perfusion loop is set at a rate adequate to allow timely equilibration of the liquid media dissolved gases with the external controlled incubator environment. Cell attachment substrates are introduced either simultaneously or sequentially with cells into the culture vessel to give an appropriate density, such as 5 mg of beads per of ml of media, of attachment substrate for the anchorage dependent cells. The culture media is then rotated about a horizontal axis. The rotation may begin at about 10 revolutions per minute, the slowest rate which produces a microcarrier bead orbital trajectory in which the beads do not accumulate appreciably at the vessel walls either by gravitational induced settling or by rotationally induced centrifugation. The vessel wall, mixing vane, and centerline spin filter are also set at the same rotation (10 RPM) in order to provide essentially no relative motion of the culture media with respect to the vessel internal surfaces and therefore producing the minimal fluid velocity gradients and fluid shear stresses in the culture fluid dynamic environment.

It is recognized that in gravity the relative motion of the rotating fluid without any particles may be reduced to a level which can not be easily preserved; however, that when particles are placed into the rotating fluid that a measurable or visual change occurs and some relative motion occurs. However, the shear stress field which results is the minimum which has been found in a bio-reactor for culturing cells or tissue and therefore, permits the creation of 3-dimensional tissue which has not heretofore been possible. This mixture of freely suspended attachment substrates within the rotating fluid media and rotating vessel components is allowed to equilibrate for a short period of time, a time sufficient for transient flows to dampen out. The media perfusion rate is set to zero during the cell loading and initial attachment (cells attaching to the microcarrier substrates) phase so as to retain the small cells within the vessel proper and not to draw them through the spin filter and external media perfusion loop where severe cell damage would occur. This initial loading and attachment phase may take 2 to 4 hours. The absence of perfusion induced mixing, nutrient delivery, waste product removal, and respiratory gas exchange during this period is well tolerated due to the small total amount of initial cellular metabolism and the brevity of this condition. The desired cells are gently injected into the rotating culture media over a short period of time, (2 minutes) so as to minimize cell damage while passing through the syringe and injection port. After injection of the cells is complete, the vessel outer wall is quickly (within 1 minute) returned to initial rotation (10 RPM) to match the angular rotational rate of the rest of the system and thereby returning the fluid shear stress field to the minimal level obtainable for these freely suspended cells and attachment substrates.

All free gas bubbles are then purged via a venting port to assure minimal disruption to the rotating fluid/substrate/cell mixture which would result from buoyant gas interfering with the near solid body rotating mixture. The cells and beads remain in nearly the same local region due to the similarity of their orbits and do not achieve a large net separation from each other. They are allowed to interact with 3-dimensional freedom for spatial orientation within the rotating fluid and are not exposed to disruptive shear stresses which would cause cell damage and limit the assembly of delicate 3-dimensional structures.

After the initial loading and attachment phase (2 to 4 hours) the perfusion loop is set at a low flow speed (4.5 ml. per minute) that does not interfere with the initial 3-dimensional assembly process. As the culture progresses the size and sedimentation rate of the assembled tissue increases, the system rotational rates must be increased (increasing in increments of about 1 to 2 RPM from about 10 to about 20 RPM or more) in order to reduce the gravitationally induced orbital distortion (from the ideal circular streamlines) of the now increased (2 millimeter) diameter tissue pieces. The rotational rate may be increased until centrifugation is observed to cause accumulation of the tissue pieces at the outer vessel walls that becomes detrimental to further 3-dimensional growth of delicate structure. The rapid cell growth and increasing total metabolic demand necessitates additional intermittent injections of nutrients. This injection is increased as necessary to maintain glucose and other nutrient levels. The culture may be allowed to progress beyond the point at which it is possible to select excellent particle orbits. At this point gravity has introduced constraints which somewhat degrades performance in terms of fully 3-dimensional low shear tissue culture.

Every 15 minutes during the total culture period the spin filter is stopped and started at 15-second intervals for 1 minute in order to clear particles from the spin filter surface. This prevents accumulation of substrates, cells, and debris on the filter. Samples of the growing tissue may be withdrawn as desired from a syringe attached to the sample port. The vessel outer wall may be temporarily stopped to allow practical handling of this syringe connected to the vessel.

EXAMPLE I

Preparation

A 3-dimensional rat bone cell culture was produced in the following manner. The bio-reactor, slow turning lateral vessel (STLV) was prepared by washing detergent and germicidal disinfectant solution (Roccal II) at the recommended concentration for disinfection and cleaning followed by copious rinsing and soaking with high quality deionized water. The bioreactor was sterilized by autoclaving then rinsed once with culture medium.

Inoculation

The 100 ml. volume STLV was filled with cell culture medium consisting of minimum essential medium (MEM) with Earle's salts, growth supplements, antibiotics and 10% fetal bovine serum. After equilibration for one hour in the $CO_2$ incubator, the substrate consisting of collagen coated dextian polymer, Cytodex 3 microcarrier beads (Pharmacia Fine Chemicals, Uppsala, Sweden) were suspended in a small volume of culture medium and loaded into the device. An empty syringe attached to one of the sampling ports functioned as a compliant volume reservoir during inoculation to receive the displaced media. The final bead concentration was 5 mg./ml. of vessel volume.

A volume of culture medium was injected to completely fill the device. All air bubbles were removed using a syringe attached to a sample port on the vessel. The device containing suspended beads was placed in a 5% $CO_2$ environment at 37.degree.C. to equilibrate for about 30 minutes.

Mono-dispersed primary rat osteoblast calvarium bone cells were suspended in a small volume of cell culture medium and inoculated into the vessel by injection through a sample port. The cell seeding density was approximately 10 cells per bead. A second syringe was attached to another port and served as a compliant volume reservoir for the vessel. The device was placed on the rotation base and connected to the air pump. The motor was switched on and the rotation rate was set at approximately 16 RPM.

Cell Attachment and Three Dimensional Growth

At 24 hours, microscopic observation showed that the cells were well attached and flattened on the surface of the beads. The beads and cells were not associated into higher order structures at this point. Very little orbital path distortion or centrifugation was observed. The medium was changed to remove non-viable floating cells. On day three, the medium was changed again to assure nutrient supply to the cells. At day four cells were in good condition. To replenish nutrients yet retain growth factors secreted by the cells, three-fourths of the medium was removed and the same volume of fresh medium was added. The same procedure was repeated on day 5.

On day 5, microscopic observation of samples showed rounded assemblies of beads that were larger than seen on the previous day. Also noted were cells spanning spaces between beads. The airflow into the device was turned up to provide more oxygen to the rapidly growing culture. At this point the assemblies were observed to fall radially inwards on the "down" side and outwards on the "upside".

On the 6th day the culture was transferred to a larger 250 ml volume STLV device. On day 8, ordered assemblies of beads were very large (1-2 mm) with 8 to 15 beads in the assemblies and more three-dimensional structure was noted. The medium was changed at this time. At this point some accumulation of the tissue assemblies was occurring at the outer vessel wall. This centrifugation effect was quite gentle.

The cells were maintained in the three dimensional structure for 17 days with additional medium changes on days 9, 10 and 12 and additions of glucose on days 11, 15 and 16. There was no evidence of mechanical damage and the size of the cell/bead assemblies did not exceed the ability of the device to suspend the particles. The assemblies were of 1 to 2 mm in size and consisted of cells of mixed morphology which may be the indicia of beginning differentiation. The run was terminated by choice of the investigators.

EXAMPLE 2

Formation of "Artificial Tissue" in Free Suspension

Preparation:

The rotating reactor vessel system (RWPV) consisting of a 500 ml cell culture vessel, a hollow fiber oxygenator, a prototype diaphragm pump, an in-line pH sensor, sample ports and a peristaltic pump for infusion of fresh medium were assembled, sterilized by ethylene oxide (ETO) and aerated for two days. The vessel was then loaded with phosphate buffered saline (PBS) to rinse and remove residual ETO. During this step, a leak was discovered in the oxygenator and unit was replaced using sterile techniques. The system was then loaded with culture medium and placed in the $CO_2$ incubator. After remaining sterile for at least two days, the RWPV system was loaded with cells and substratum as described below.

Inoculation

Cytodex 3 microcarrier beads (Pharmacia Fine Chemicals, Uppsala, Sweden) were reconstituted according to standard laboratory procedures, suspended in Microcarrier Medium (MM), containing 20% fetal calf serum, 100 units of penicillin/ml and 100 ug of streptomycin/ml, loaded into a 50 ml syringe and injected into the vessel. The bead density in the vessel was 5 mg/ml of vessel volume.

The system was then loaded with Baby Hamster Kidney (BBK21) cells at passage level 56. To achieve this, ampules of frozen stock BHK21 cells were thawed. The cells were suspended in 50 ml of growth medium (MM) and put into a 20 ml syringe for injection into the culture vessel. The final cell seeding density was approximately 6 cells/bead. Cells were loaded into the vessel at 9:30 AM.

The system parameters were as follows. The constant volume diaphragm pump was timed to circulate the medium at 4.5 ml/min. The pump rate was turned up to 20 mi/min four days after addition of cells and beads in order to increase the oxygen delivery to the reactor vessel. The pump system delivered 0.7 ml every two seconds. The rotation rate of the vessel and the mixing blades were set at 15 to 20 RPM and remained there during the test. The spin filter rotation rate was 25 to 30 RPM. This produced a very low turbulence environment resulting in a cell/bead suspension upon introduction of those particles.

Cell Attachment and Three Dimensional Growth:

In order to assess the rate of attachment of cells to the substrate beads, samples of the cell-bead suspension were removed for cell counts and microscopic observation at 2, 4 and 6 hours after loading the vessel with cells. Many of the cells attached to the beads within two hours and flattened on the surface of the beads which is an essential state preliminary to growth of the cells. Early in this test microscopic observation showed that some of the mono-dispersed cells clumped in groups of 10 to 30 cells. There did not appear to be any mechanical damage or damage due to cells striking the vessel wall. At 4 hours, these clumps of cells had attached to beads and were flattened on the surfaces. No orbital distortion or centrifugation effects were visible at this point.

At 24 hours some beads were covered with cells but there were also many floating cells. At this time, fresh medium was perfused into the vessel. Four hours later, almost all of the cells had attached to beads and there was no evidence of cell-cell aggregates as seen earlier. The poor appearance at 24 hours was probably due to toxicity from the new oxygenator used to replace the original one that leaked during set up.

At 48 hours the cell growth rate began to increase rapidly. Glucose, glutamine (nutrients) and sodium hydroxide for pH control were added on day four to compensate for cell metabolism and depletion of nutrients.

At five days, aggregates of cells and beads were noted and the medium was changed to a low percent serum (2%) medium to slow cell metabolism and growth. The cells continued to grow, however, and reached a maximum density of 148 cells/bead at day 7. Very large and uniformed assemblies of about 1 to 2 mm formed and did not disaggregate during the remainder of the test. Ordered uniform assemblies of 8 to 10 beads formed in 3 dimensional arrays over which the cells grew into a smooth membrane-like configuration of elongated fibroblastoid morphology. Multiple layers of these cells were apparent by microscope examination both on the surface and in the inter-bead spaces. The cells were placed in ordered layers with cell membranes immediately adjacent to each other. The test was terminated at 10 days. The size of most of the tissue-like aggregates of cells on beads did not exceed the limits of the rotating wall vaned vessel to freely suspend the aggregates in a quiescent 3-dimensional environment, unrestricted by internal boundaries. Some very large assemblies, 3 to 8 mm, were observed. These rapidly sedimenting tissues were observed to exhibit grossly distorted orbital paths and centrifugation to the outer vessel walls. High-energy impacts and vigorous "rolling" effects were observed. These were considered beyond the process capacity to retain the quiescent, low shear, 3-dimensional culture environment.

Having fully described this new and unique invention,

We claim:

1. In a method for culturing mammalian cells to produce in vitro multi-cellular, three-dimensional assemblies of predominately living mammalian cells with predominately adjacent cell membranes evidencing minimal mechanical damage, said method including the steps of:

providing a bioreactor having a culture chamber rotatable about an approximately horizontal longitudinal axis, means to controllably rotate said culture chamber, means to introduce an oxygen-containing fluid throughout said culture chamber and means to remove metabolic waste products therefrom;

filling said culture chamber completely with a fluid nutrient media, cell attachment substrates, and mammalian cells of a single type, to establish a culturing environment;

rotating said culture chamber about its longitudinal axis while introducing an oxygen-containing fluid to said culture chamber and removing metabolic waste products therefrom to maintain said culturing environment;

controlling the rotation of said culture chamber such that the fluid medium except during transient periods as the following simultaneous properties:

a. localization of cells and attachment substrates with similar or differing sedimentation properties in a similar spatial region, b. freedom for three dimensional spatial orientation or assemblies formed by the culturing of the cells, c. low shear and essentially no relative motion of said culturing environment with respect to the boundaries of the chamber; and determining the trajectory of the assemblies, in response to said determining step:

increasing the speed of rotation of the culture chamber if the assemblies fall excessively inward and downward on the downward side of the rotation cycle and excessively outward and insufficiently upward on the upgoing side of the rotation cycle to prevent wall impact; or decreasing the speed of rotation of the culture chamber in response to excessive accumulation of the assemblies near the outer wall of the culture vessel so as not to restrict three dimensional assembly, and as the size of the assemblies increase beyond the capability to fully satisfy the above three properties by further increase of the speed of rotation, selecting a rotational rate to visually obtain minimal collision frequency and intensity, the improvement comprising:

subjecting the contents of the culture chamber to a time varying electromagnetic force driven by a pulsed square wave exerting a magnetic field of from about 0.05 to 0.5 gauss while culturing the cells in the chamber, wherein the magnetic field varies over time and can be any value within the range of from about 0.05 to 0.5 gauss.

2. In a method for growing mammalian cell cultures comprising the step of providing a bioreactor having a culture chamber formed of a coaxial tubular housing, intermediate circumferentially disposed blades and a central tubular filter about a common horizontal axis of rotation each being independently rotatable of one another;

disposing a fluid nutrient medium having a first density, mammalian cells, and discrete suspension materials having a different density from the density of the fluid nutrient medium in said culture chamber;

controlling the rotation of said culture chamber and thereby the fluid nutrient medium for placing the mammalian cells and the discrete suspension materials in suspension at discrete spatial locations in the fluid nutrient medium and out of an interference relationship with one another by virtue of the rotation;

introducing a controlled input of fresh fluid nutrient medium to said culture chamber and removing a controlled output of fluid nutrient medium from said culture chamber while said fluid nutrient medium in said culture chamber is rotated about said axis of rotation, the improvement comprising:

subjecting the contents of the culture chamber to a time varying electromagnetic force driven by a pulsed square wave exerting a magnetic field of from about 0.05 to 0.5 gauss while culturing the cells in the chamber, wherein the magnetic field varies over time and can be any value within the range of from about 0.05 to 0.5 gauss.

3. The method set forth in claim 2 wherein the rotation of the central tubular filter is intermittently at a different rotational speed than the tubular housing to create a transient shear stress thereby clearing the surface of the central tubular filter and preventing clogging.

4. The method set forth in claim 2 wherein the rotation of the circumferentially disposed blades is a different rotational speed than the tubular housing to assist the discrete suspension materials and the mammalian cells to maintain their spatial locations.

5. The method set forth in claim 2 wherein, when the rotation of the tubular housing is stopped, the circumferentially disposed blades may be rotated to maintain the discrete suspension materials and the mammalian cells in suspension.

6. In a method for growing mammalian cell cultures comprising the steps of providing a bioreactor having a housing completely filled with a fluid nutrient medium with a first density, mammalian cells, and discrete suspension materials having a different density from the density of the fluid nutrient medium and rotating the housing about a rotational axis; controlling the rotation of the fluid nutrient medium for placing the discrete suspension material and mammalian cells in suspension at discrete spatial locations in the fluid nutrient medium and out of an interference relationship with one another by virtue of the rotation of the fluid nutrient medium and axis of rotation; while rotating the housing containing the fluid nutrient medium, radially introducing fresh fluid nutrient medium into the housing at a second input location where said first input location and said second input location are at opposite ends of the housing and located adjacent the rotational axis, while removing fluid nutrient medium from a location intermediate of said first and said second input location so that the flow of fluid medium is toroidal from each end of the housing, the improvement comprising:

subjecting the contents of the culture chamber to a time varying electromagnetic force driven by a pulsed square wave exerting a magnetic field of from about 0.05 to 0.5 gauss while culturing the cells in the chamber, wherein the magnetic field varies over time and can be any value within the range of from about 0.05 to 0.5 gauss.

7. The method as set forth in claim 6 and further including the step of:

maintaining the input and output volume of fluid nutrient medium such that there is no head space in the housing.

8. The method as set forth in claim 6 wherein the rotation of the housing is at a rate of rotation to minimize the velocity gradient between the inner wall of the housing and the fluid nutrient medium.

9. The method as set forth in claim 6 and further including the step of recirculating the removed fluid medium to said first input location and further including the step of introducing constituent materials to the fluid medium prior to introducing fluid nutrient medium into the housing.

10. The method set forth in claim 6 wherein said bioreactor further includes a central tubular filter and wherein the removal of the fluid nutrient medium is accomplished by intermittently having a different rotational speed of the central tubular filter than the rotational speed of the tubular housing to create a transient shear stress thereby clearing the surface of the central tubular filter.

11. In a method for growing cell cultures comprising the steps of providing a bioreactor formed of a tubular housing completely filled with a fluid nutrient medium discrete suspension materials, and mammalian cells are disposed in the fluid nutrient medium and rotating said housing about a horizontal rotational axis;

controlling the rotation of the fluid nutrient medium for placing the discrete suspension materials and the mammalian cells in suspension at discrete spatial locations in the fluid nutrient medium and out of an interference relationship with one another by virtue of the rotation of the fluid nutrient medium and horizontal axis of rotation; while rotating the housing containing the fluid nutrient medium, introducing fresh fluid nutrient medium into the housing at input locations, one adjacent each end of the housing, while removing fluid nutrient medium from the housing at another location, such input being radially discharged relative to the rotational axis whereby fluid turbulence resulting from the incoming fluid nutrient medium is maintained at a minimum thereby setting up a flow field which is toroidal from each end of the housing, the improvement comprising:

subjecting the contents of the culture chamber to a time varying electromagnetic force driven by a pulsed square wave exerting a magnetic field of from about 0.05 to 0.5 gauss while culturing the cells in the chamber, wherein the magnetic field varies over time and can be any value within the range of from about 0.05 to 0.5 gauss.

12. The method as set forth in claim 11 wherein, when the rotation of the tubular housing is stopped, the discrete suspension materials and the cells are maintained in suspension by rotation of a pair of circumferentially disposed blades.

13. A method for culturing mammalian cells in a bioreactor comprising the steps of:

a. placing a fluid culture medium and at least one cell in a cell culture reactor vessel to initiate a cell culture environment;

b. rotating the culture reactor vessel via a means for rotating the culture vessel about a horizontal central axis at a rotation speed;

c. controlling the rotation of the culture reactor vessel by adjusting the rotation speed to maintain the ccli culture environment; and d. exposing the cells to a time varying electromagnetic force driven by a pulsed square wave exerting a magnetic field of from about 0.05 to about 0.5 gauss, wherein the magnetic field varies over time and can be any value within the range of from about 0.05 to 0.5 gauss.

14. The method of claim 13, wherein the cell culture environment has the properties of collocation of the fluid culture medium and the cells, essentially no relative motion of the fluid culture medium with respect to the culture reactor vessel, and freedom for the three dimensional spatial orientation of the cells.

15. The method of claim 13, wherein the cell culture environment is maintained by perfusion.

16. The method of claim 13, wherein the fluid culture medium has a main fluid flow loop comprising a supply manifold, a pump, an oxygenator, a cell culture reactor vessel, and a waste.

17. The method of claim 13 wherein the bioreactor is located in unit gravity.

18. The method of claim 13 wherein the bioreactor is located in microgravity.

19. The method of claim 13, wherein the fluid culture medium comprises a cell attachment substrate.

20. The method of claim 13 wherein the rotation speed is from about 5 to about 100 RPM.

21. The method of claim 13, wherein the method is carried out in unit gravity.

22. The method of claim 13 wherein the method is carried out in less than unit gravity.

* * * * *